United States Patent [19]

Fischer

[11] Plant 4,846

[45] May 11, 1982

[54] AFRICAN VIOLET NAMED JACKIE

[75] Inventor: Arnold W. Fischer, Hanover, Fed. Rep. of Germany

[73] Assignee: Pan-American Plant Company, West Chicago, Ill.

[21] Appl. No.: 15,356

[22] Filed: Feb. 26, 1979

[51] Int. Cl.[3] ..... A01H 5/00

[52] U.S. Cl. ..... Plt./69

[58] Field of Search ..... Plt./69

*Primary Examiner*—Robert E. Bagwill

*Attorney, Agent, or Firm*—Charles W. Rummler

[57] ABSTRACT

A new African violet distinguished by its vigorous growth and its continuous and profuse production of dark blue flowers borne as a bouquet above foliage of a light green color, the dark violet color of the blooms being highlighted by the bright yellow anthers at the center of each flower to make a strikingly attractive display.

1 Drawing Figure

BACKGROUND OF THE NEW PLANT

This African violet cultivar was discovered by me in 1974 as a seedling of unknown parentage growing in my greenhouse at Hanover, Germany, among breeding stock maintained by me for use in developing improved violets for the commercial market. This plant attracted me because of its vigorous growth and many flowers of large size and beautiful color and I propagated this plant, by means of leaf cuttings, through several successive generations to test its ability to retain its distinctive features. It was thus determined that this new plant not only retained its novelty from generation to generation but also had the characteristics suitable for commercial realization. Commercial scale propagation, by means of cuttings, is now being done at West Chicago, Ill., U.S.A.

DESCRIPTION OF THE DRAWING

My new African violet plant is illustrated by the accompanying photographic drawing which, in full color, shows a typical potted plant in full bloom, the color rendition being as nearly true as is reasonably possible to obtain through conventional professional photographic procedures.

DESCRIPTION OF THE NEW PLANT

The following is a detailed description of my new African violet plant based upon observations of greenhouse plants grown at West Chicago, Ill., U.S.A., the color designations being according to The R.H.S. Colour Chart published by The Royal Horticultural Society of London, England.

THE PLANT

Origin: Seedling.
Parentage: Unknown.
Classification:
- *Botanic.*—*Saintpaulia ionantha.*
- *Commercial.*—African violet potted plant.

Form: Compact rosette.
Growth: Vigorous and strong with a rapid growth rate.
Foliage:
- *Quantity.*—Abundant with about 13 leaves.
- Size of leaf.—From very small to about 8.2 cm. in length and 7.5 cm. in width.

- *Leaf shape.*—Oval with an acute apex and repand to sinuate margin.
- *Texture.*—Pubescent.
- *Aspect.*—Glossy.
- Color.—Upper side — 137A. Under side — 138A.
- *Ribs and veins.*—Pinnate.
- *Petioles.*—Length — From insignificant to about 6.5 cm. depending upon age of leaf.

THE BUD

Form: Vase shaped.
Size: Variable in both diameter and length.
Opening rate: Average for typical African violet plants.
Color of petals:
- *When sepals first divide.*—80B.
- *When petals begin to unfurl.*—89A.

Sepals:
- *Number.*—Five.
- *Shape.*—Branched and lanceolate becoming flat when flowers open.
- *Color.*—Inside — 147C. Outside — 147C.

Calyx:
- *Size.*—Small.
- *Shape.*—Calyx splits to star shape.
- *Aspect.*—Hairy.

Peduncle:
- *Length.*—From about 5.5 to 5.8 cm.
- *Strength.*—Erect and rigid.
- *Aspect.*—Hairy.
- *Color.*—177C.

THE FLOWER

Blooming habit: Profuse and continuous.
Borne: As a cyme.
Size of flower: Large; about 4 cm. in diameter.
Shape of flower: Cup shaped when bloom first opens and becoming flat as the bloom matures.
Petalage: 5 petals in rotate and sympetalous arrangement.
- *Form.*—Zygomorphic with sinuate margin and rounded apex.
- *Color.*—Top side — 89A. Reverse side — 87B.
- *Texture.*—Soft.
- *Appearance.*—Satiny.

Main stem: Length — about 5.5 to 5.8 cm.
- *Strength.*—Strong and upright.
- *Color.*—177C.

Persistence: Flowers hang on and dry.
Fragrance: None.
Lasting quality: From 10 to 20 days.

REPRODUCTIVE ORGANS

Stamens:

*Anthers.*—Two in number in monadelphous arrangement.

*Filaments.*—Length — about 3 mm. Color: Violet to yellow.

*Pollen.*—Color — Yellow.

Pistils: One only.

*Style.*—Length — about 5.6 mm. Color: Violet.

*Stigma.*—Color — Violet.

Ovaries: Hypogynous and tomentose.

This African violet plant is particularly distinguished by its vigorous growth and profusion of blooms borne on sturdy, erect peduncles in a bouquet above broad foliage of a light green color. The flower form is zygomorphic, typical of African violets, and the corolla is rotate and sympetalous with three larger and two smaller petals. The dark violet color of the blossoms is highlighted by the bright yellow anthers in each blossom center making the total display strikingly attractive.

I claim:

1. A new African violet cultivar, substantially as herein shown and described, characterized by its profuse production of dark blue flowers borne as in a bouquet above the foliage on sturdy, erect stems.

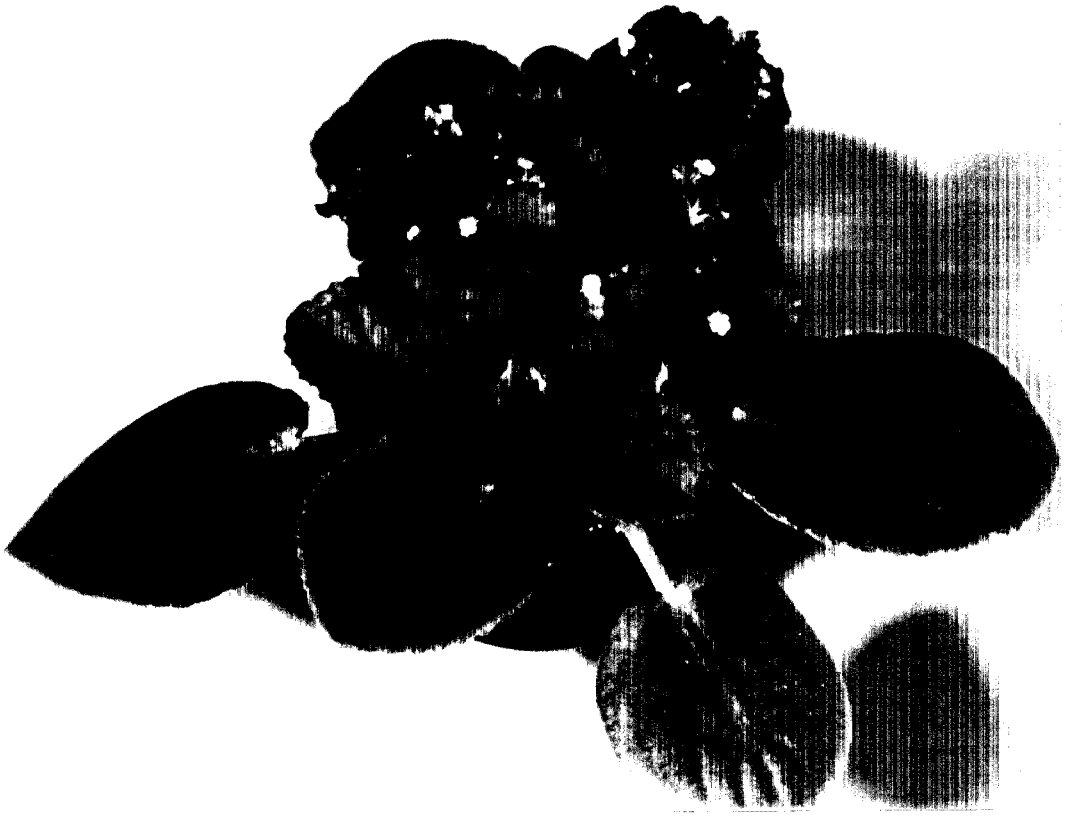

* * * * *